United States Patent [19]
Roberts et al.

[11] Patent Number: 5,202,494
[45] Date of Patent: Apr. 13, 1993

[54] CONTINUOUS PROCESS FOR THE PRODUCTION OF DISULFIDES

[75] Inventors: John S. Roberts; Harold R. Hunt, both of Bartlesville; Charles A. Drake, Nowata, all of Okla.

[73] Assignee: Phillips Petroleum Company, Bartlesville, Okla.

[21] Appl. No.: 531,289

[22] Filed: May 31, 1990

[51] Int. Cl.$^5$ ............................................. C07C 319/24
[52] U.S. Cl. ....................................... 568/26; 208/189
[58] Field of Search .................. 568/26; 208/189, 207

[56] References Cited

U.S. PATENT DOCUMENTS

| | | | |
|---|---|---|---|
| 2,083,917 | 6/1937 | McGee | 208/189 |
| 3,022,351 | 2/1962 | Mihm et al. | 568/26 |
| 4,564,709 | 1/1986 | Koyama et al. | 568/26 |

OTHER PUBLICATIONS

J. Schutten et al., Chemical Abstracts, vol. 93, No. 187238u (1980). Macroporous styrene–divinylbenzene copolymers.
J. Schutten et al., Angew. Makromol. Chem., vol. 89, pp. 201–219 (1980). Macroporous Styrene-Divinylbenzene Copolymers as Carriers for Poly(vinylamino)-Cobaltphthalocyanine Oxidation Catalysts.
"The Chemical Thermodynamics of Organic Compounds", D. A. Stull, E. J. Westrum, Jr. and G. C. Sinke (1969) Chapter 14.
"Basic Principles and Calculattions in Chemical Engineering", Second Edition, D. M. Himmelblau, (1967) Appendix F.

*Primary Examiner*—Mary E. Ceperley
*Attorney, Agent, or Firm*—Gary L. Haag

[57] ABSTRACT

Process and apparatus for continuous production of disulfides by reacting at least one mercaptan and oxygen in the presence of a suitable catalyst selected from the group consisting of an alkaline earth metal oxide alone or in combination with an alkali metal oxide, on a refractory support, or a basic form of macroreticular polystyrene-divinyl benzene copolymer.

21 Claims, 1 Drawing Sheet

CONTINUOUS PROCESS FOR THE PRODUCTION OF DISULFIDES

BACKGROUND OF THE INVENTION

This invention relates to a new and useful method for the continuous production of disulfides.

Disulfide compounds are used in the manufacture of pesticides, rodent repellants, insecticides, and in pharmaceutical synthesis. They are also used as additives in greases and diesel fuels.

The production of disulfides is well known in the art. The goal in producing disulfides is to obtain products of high purity in high yields, at the most economical cost. It is also desired that the methods and/or processes employed In such production be unhazardous and environmentally safe. Unfortunately, the prior art methods do not satisfy these goals to the extent that either safety, purity, yield, and/or cost is compromised when any of the known methods is used.

This invention by avoiding and/or substantially minimizing the aforementioned problems of the prior art, represents a new, useful, and improved continuous process for producing disulfides using various catalysts.

SUMMARY OF THE INVENTION

It is an object of this invention, to provide for the continuous production of disulfides.

It is also an object of this invention to provide for the continuous production of disulfides using a catalyst system comprising an alkaline earth metal oxide and alkali metal oxide impregnated on a refractory metal oxide support.

It is another object of this invention to provide for the continuous production of disulfides using an alkaline earth metal oxide catalyst on a refractory metal oxide support.

It is a further object of this invention to provide for the continuous production of disulfides using basic macroreticular polystyrene-divinyl benzene co made and sold by Rohm and Haas under the trademark "AMBERLYST A-21" catalyst.

In accordance with this invention, a continuous process is provided for the production of disulfides by contacting at least one mercaptan and oxygen in the presence of a suitable catalyst.

In FIG. 1, there is illustrated schematically a process embodying the invention.

DETAILED DESCRIPTION OF THE INVENTION

Figure 1:
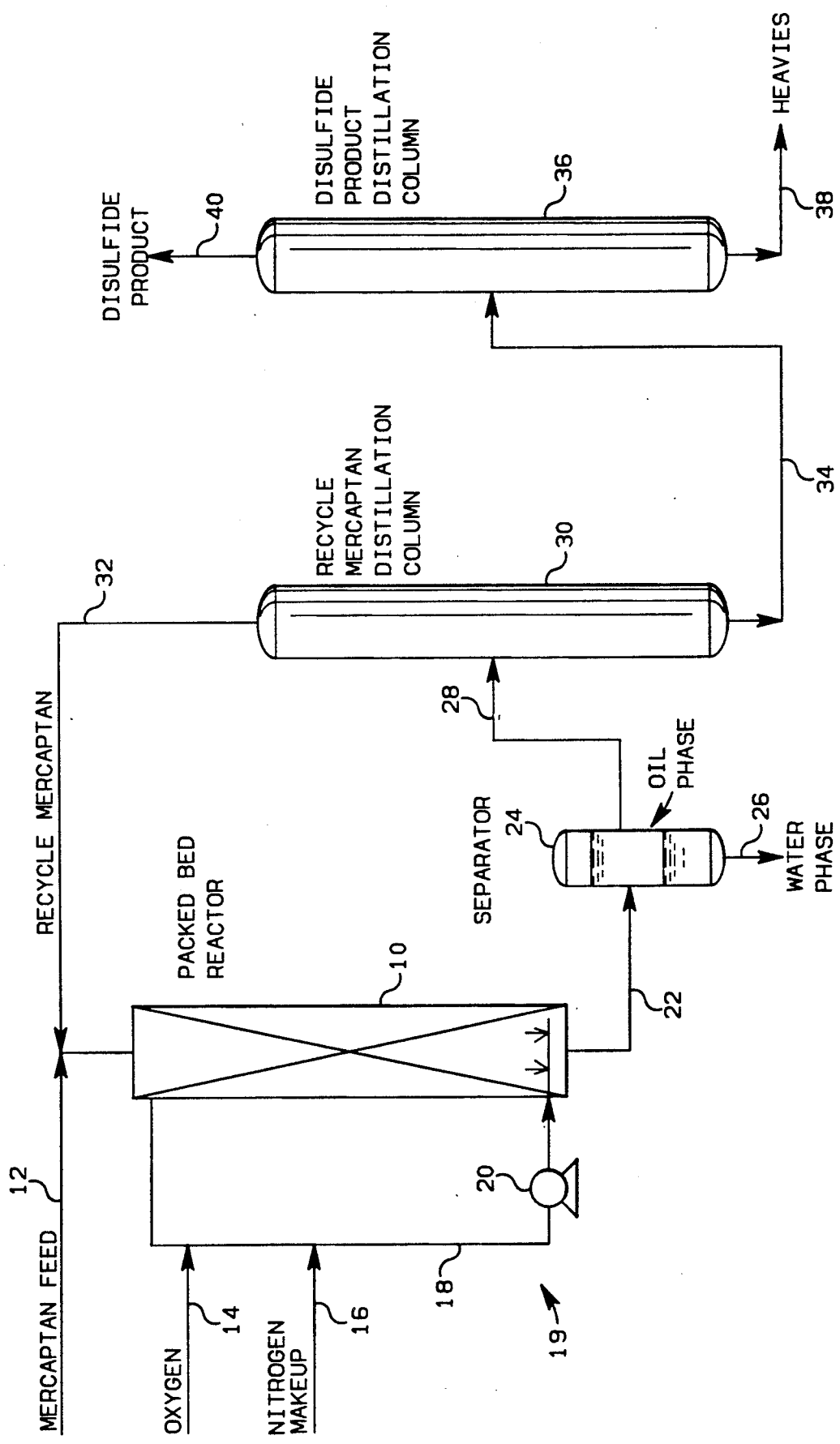

The ingredients useful in carrying out this invention comprise mercaptans, an inert diluent, oxygen, and suitable catalyst(s). The process of the invention is further illustrated by FIG. 1 and the accompanying description thereof.

Broadly speaking, there are, at least, three separate preferred embodiments of this invention. These embodiments use different catalysts selected from the group consisting of an alkaline earth metal oxide alone or in combination with an alkali metal oxide, on a refractory support, and "AMBERLYST A-21" catalyst.

However, these embodiments are practiced by utilizing the same general process In very simplified terms, this process essentially involves contacting air or oxygen diluted with an inert gas, with mercaptan, in the presence of a suitable catalyst. Special features of this process include but are not limited to, introducing the air or oxygen/nitrogen in a manner countercurrent to the mercaptan flow, and recycling the nitrogen, unreacted oxygen, and unreacted mercaptans.

The mercaptans useful in this invention broadly include those with 1 to 18 carbons in which the mercaptan can be located on a primary, secondary, tertiary or aromatic carbon. Examples of this group of mercaptans include but are not limited to, t-butyl mercaptan, t-dodecyl mercaptan, t-octyl mercaptan, t-hexadecyl mercaptan isopropyl mercaptan, sec-butyl mercaptan, sec-dodecyl mercaptan, methyl mercaptan, n-propyl mercaptan, n-butyl mercaptan, n-amyl mercaptan, n-hexyl mercaptan, n-octyl mercaptan, n-dodecyl mercaptan, n-octadecyl mercaptan, thiophenol, benzyl mercaptan, cyclohexyl mercaptan, and cyclopentyl mercaptan.

However, the preferred mercaptans for purposes of this invention are those with the mercaptan still attached to a primary, secondary, or aromatic carbon, and having 1 to 12 carbon atoms. Examples of this class of compounds are isopropyl mercaptan, sec-butyl mercaptan, sec-dodecyl mercaptan, methyl mercaptan, n-propyl mercaptan, n-butyl mercaptan, n-amyl mercaptan, n-hexyl mercaptan, n-octyl mercaptan, n-dodecyl mercaptan, n-octadecyl mercaptan, thiophenol, benzyl mercaptan, cyclohexyl mercaptan, cyclopentyl mercaptan, and like compounds.

Most particularly preferred are those mercaptans with 1 to 8 carbon atoms, with the mercaptan attached to either a primary or an aromatic carbon atom. Examples of this class of compound are methyl mercaptan, n-propyl mercaptan, n-butyl mercaptan, n-amyl mercaptan, n-hexyl mercaptan, n-octyl mercaptan, n-dodecyl mercaptan, n-octadecyl mercaptan, thiophenol, benzyl mercaptan, and similar compounds.

Generally, any inert gas is useful as a diluent in this process. Examples of such inert gases are helium, argon, neon, and other Group VIII members of the periodic table. Particularly preferred, though, is nitrogen.

The oxygen useful in this invention can be atmospheric oxygen. Preferred, however, is elemental oxygen.

Various catalysts are useful in this invention. Such catalysis include alkaline earth metal oxides alone or in combination with alkali metal oxides, or mixtures of these oxides, on a suitable refractory metal oxide support.

Of the alkaline earth metals, magnesium is the most preferred. Likewise sodium is the most preferred of the alkali metals. These metal oxide catalysts can be either commercially obtained or prepared by conventional methods known in the art. One such method is by calcining the carbonate, acetate, nitrate, hydroxide, or other suitable salts of the desired metal.

Refractory metal oxide supports typically useful in carrying out this invention include but are not limited to alumina, silica, silica-alumina, titania, and the like. Alumina, however, is the preferred support.

It is noted that the catalyst combination of MgO/Na$_2$O on alumina support is the most preferred catalyst for carrying out this invention. Also preferred is MgO catalyst on a refractory metal oxide support.

Another suitable catalyst for this invention is the class of basic macroreticular polystyrene-divinyl benzene copolymers, such as those manufactured by Rohm and Haas, and sold under the trademark "AMBERLYST A-21".

There are, in general, at least, three separate preferred embodiments of this invention. In the first embodiment, a process is provided for the continuous production of disulfides using a catalyst comprising of magnesium oxide and sodium oxide impregnated on alumina support. In the second embodiment, a process is provided for the continuous production of disulfides using magnesium oxide catalyst on alumina support. In the third embodiment, a process is provided for the continuous production of disulfides using "AMBERLYST A-21" catalyst.

These various embodiments, however, use the same general process in which the desired catalyst is contained in a reactor. The mercaptan is introduced through the top portion of the reactor. Air or oxygen diluted with an inert gas, preferably nitrogen, is introduced into the reactor in a manner countercurrent to the mercaptan flow. The oxygen can be introduced at various points as a means of distributing the heat of reaction throughout the reaction bed. This countercurrent flow maximizes contact between the oxygen, catalyst, and mercaptan. It is desirable that the oxygen be continuously diluted with nitrogen as a means of controlling reaction temperatures. It is also desirable that both the nitrogen and any unreacted oxygen be continuously recycled. Typically, this recycling is facilitated by means of a compressor, blower, or other suitable device, which is conveniently attached to the reactor.

The general ranges of ingredients and reaction conditions suitable for carrying out the invention are as follows: mercaptan feed velocities are in the range of about 0.01 to about 10 g feed/g catalyst-hr Weight Hour Space Velocity (WHSV) with a preferred range of 0.1 to 1/hr. Oxygen feed velocities are generally in the range of from about 0.01 to about 100/ml oxygen/g catalyst hour Gas Hourly Space Velocity (GHSV) and more preferably in the range from about 0.1 to about 10 ml/g-hr GHSV. The midbed temperature for this reaction generally ranges from about 20° C. to about 150° C. However, a temperature range of from about 80° C. to about 120° C. is preferred. The pressure in the packed reactor bed generally ranges from about 0 psig to about 500 psig (about 1 to about 35 atmospheres), but more preferably in the range from about 0 psig to about 150 psig (about 1 to about 11 atmospheres).

The reaction of the invention usually proceeds at a fast rate and is a more complete reaction relative to those disclosed in the prior art. This improved reaction is attributable to the catalysts and process used.

The products of the reaction which include disulfides, unreacted mercaptans, and water are conducted to a separating device. At this point, these products are separated into an oil phase and a water phase. The oil phase is further conducted to a mercaptan distillation device from which unreacted mercaptans are recycled overhead back into the reactor. The disulfide product is conducted to a distillation column where the "heavies" consisting of polysulfides and other undesirable by-products with greater molecular weights than the desired disulfide are separated out and the purified disulfide product is collected. The collected disulfide product can be analyzed using conventional methods known in the art.

Referring now to FIG. 1, there is schematically illustrated an apparatus useful in the practice of the invention. A packed catalyst bed reactor 10 has operably attached thereto:

(a) a mercaptan feed conduit 12 for feeding mercaptan into the packed reactor 10;

(b) an oxygen conduit 14 in communication with a suitable oxygen source;

(c) a nitrogen conduit 16 in communication with a suitable nitrogen source;

(d) a conduit means 18 for oxygen and nitrogen circulation to and from the reactor 10; and (e) a pressure regulating and/or maintenance device such as a blower or compressor 20 operably associated with the conduit means 18 to form a gas recycling means 19.

The reactor 10 is linked by means of a product conduit 22 to a separator device 24. The separator device 24 has a water phase outlet conduit 26 operably attached to its bottom portion, and an oil phase conducting conduit 28 operably attached to or near its top portion to provide communication with a mercaptan distillation device 30. Attached to the top of the mercaptan distillation column 30 and leading to the top of the reactor 10, is a recycle mercaptan conduit 32 for recycling unreacted mercaptans to the reactor 10. Attached to the bottom portion of the mercaptan distillation column 30 is a product conduit 34, for unpurified disulfide products, in communication with a disulfide distillation device 36. Operably attached to the bottom portion of the disulfide distillation device is a conduit 38 for separating out the heavies. In communication with the disulfide distillation device 36, is a collecting device 40 for the purified disulfide product.

In operation, the desired catalyst is first introduced into the reactor 10. Mercaptan is then fed into the reactor 10, via the mercaptan feed conduit 12. Oxygen is fed into the reactor 10 via the oxygen conduit 14 while nitrogen is fed into the reactor via the nitrogen conduit 16. Feeding these ingredients in the manner described above and illustrated in FIG. 1 facilitates countercurrent contacting of mercaptan and oxygen. Recycling of nitrogen and unreacted oxygen is accomplished via the joint effort of the circulation conduit 18 and the blower or compressor 20.

The remnants of the oil phase containing impure disulfide are conducted via the impure disulfide conduit 34 to the disulfide distillation device 36. Purified disulfide is collected with the aid of the disulfide collecting device 40, while the heavies are separated out of the disulfide distillation device via the separation conduit 38.

The following illustrative examples further detail the various aspects of this invention.

EXAMPLE I

Preparation of Catalyst

A catalyst suitable for use in the process of the present invention was prepared by mixing 300 g alumina with 225 g magnesium nitrate and 12 g sodium nitrate in 370 ml water. The mixture was allowed to soak followed by calcination for 3 hours at 400° C. The process resulted in magnesium oxide and sodium oxide impregnated onto alumina support for use in the invention.

EXAMPLE II

To a water cooled stainless steel tubular reactor, 93.7 g of the catalyst prepared as described in Example I was added. The feedstock methyl mercaptan (MeSH) was continuously fed to the reactor at weight hourly space velocities (WHSV) and flow rates indicated in Table I.

Oxygen was introduced into the reactor at various gas hourly space velocities and flow rates shown in Table I. Nitrogen was also introduced into the reactor. The temperature of the reactor was controlled by cooling water to about 80° C. at the midbed of the reactor. The reaction pressure was maintained at about 94 psig. The product stream discharged at the bottom of the reactor contained dimethyl disulfide and unreacted methyl mercaptan. The impure dimethyl disulfide was purified by using a distillation column, and the purified product was collected. The percent conversion of the starting mercaptans was as shown in Table I and was determined on the basis of oxygen utilized in each run.

TABLE I

Continuous Production of Dimethyl Disulfide Catalyzed by $MgO/Na_2O$

| | Feedstock | | | | | |
|---|---|---|---|---|---|---|
| | Methyl mercaptan | | Oxygen | | | |
| Run | Flow rate (moles/min) | WHSV ($hr^{-1}$) | Flow rate (moles/min) | GHSV (ml/g-hr) | Mole ratio ($MeSH/O_2$) | Conversion[a] (%) |
| 1 | 0.0231 | 0.71 | 0.0044 | 62.4 | 5.25 | 4.9 |
| 2 | 0.0342 | 1.05 | 0.0044 | 62.4 | 7.77 | 41.9 |
| 3 | 0.0200 | 0.61 | 0.0022 | 31.2 | 9.09 | 42.0 |
| 4 | 0.0229 | 0.708 | 0.0022 | 31.2 | 10.42 | 62.3 |
| 5 | 0.0298 | 0.915 | 0.0009 | 11.8 | 33.10 | 76.0 |
| 6 | 0.0204 | 0.628 | 0.0009 | 11.8 | 22.67 | 92.1 |
| 7 | 0.0134 | 0.413 | 0.0009 | 11.8 | 14.89 | 82.5 |

[a]The conversion is based on molecular oxygen.

The results shown in Table I above indicate that a molar ratio of MeSH to $O_2$ of at least greater than 5.25, preferably at least about 7, is required in order to obtain a high conversion. Runs 4-7 of Table I, further indicate that an MeSH to $O_2$ molar ratio of from about 15 to 33 is the optimal range for carrying out this invention. In Run 7, with a molar ratio ($MeSH/O_2$) of 14.98, the yield was 82.5% which was increased to 92.1% by an increased $MeSH/O_2$ ratio of 22.67 as shown in Run 6.

EXAMPLE III

This example illustrates that dimethyl disulfide can also be prepared continuously using magnesium oxide as catalyst The feedstock methyl mercaptan and oxygen were continuously fed to the reactor using the same procedures and apparatus as in Example II except for the substitution of magnesium oxide as catalyst. The results are shown in Table II.

TABLE II

Continuous Production of Dimethyl Disulfide Catalyzed by MgO

| | Feedstock | | | | |
|---|---|---|---|---|---|
| | Methyl mercaptan | | Oxygen | | |
| Run | Flow rate (moles/min) | WHSV ($hr^{-1}$) | Flow rate (moles/min) | GHSV (ml/g-hr) | Conversion[a] (%) |
| 8 | 0.0237 | 0.478 | 0.0005 | 6.6 | 8.20 |
| 9 | 0.0300 | 0.648 | 0.0047 | 66.9 | 9.74 |
| 10 | 0.0304 | 0.614 | 0.0047 | 66.9 | 19.29 |

[a]The conversion is based on molecular oxygen.

The results shown in Table II demonstrate that MgO is useful as a catalyst for the continuous conversion of MeSH to dimethyl disulfide. A comparison of the results shown in Tables I and II suggests that MgO is less effective than $MgO/Na_2O$ on alumina as a catalyst useful in the practice of this invention.

EXAMPLE IV

To a water cooled stainless steel tubular reactor, 53.2 g of "AMBERLYST A-21" catalyst which had been washed with acetone and dried in a 40° C. vacuum oven was added. N-butyl mercaptan liquid feed stock was then continuously fed to the reactor at a rate of 0.64/hr liquid hourly space velocity. Atmospheric oxygen (air) was also continuously introduced at 4.2/hr gas hourly space velocity. The temperature of the reactor was controlled by water cooling to 62° C. at the midbed of the reactor. The reaction pressure was maintained at about 50-60 psig (about 4 atmospheres). Reaction product, dibutyl mercaptan, was discharged at the bottom of the reactor Analysis showed a 50.7% conversion, based on the utilization of a n-butyl mercaptan.

This example demonstrates that a dialkyl disulfide can also be made continuously employing a basic macroreticular polystyrene-divinyl benzene copolymer, "AMBERLYST A-21" catalyst.

While this invention has been described in detail for the purpose of illustration, it is not to be construed as limited thereby but is intended to cover all changes and modifications within the spirit and scope thereof.

That which is claimed is:

1. A continuous process for making disulfides comprising continuously reacting a mercaptan-based feedstream and an oxygen-bearing feedstream in the presence of a catalyst selected from the group consisting of (a) alkaline earth metal oxides on a refractory metal oxide support, (b) alkaline earth metal oxides and alkali metal oxides in combination on a refractory metal oxide support, and (c) a polymer consisting essentially of a basic form of macroreticular polystyrene-divinyl benzene copolymer thereby producing a continuous disulfide product stream and a depleted oxygen-bearing stream.

2. A process according to claim 1 wherein said mercaptan-based feedstream consists essentially of mercaptans having 1 to 12 carbon atoms per molecule.

3. A process according to claim 1 wherein said oxygen-bearing feedstream consists essentially of oxygen and in inert gas, said oxygen-bearing feedstream is contacted countercurrently with said mercaptan-based feedstream, and said process further comprising recycling said depleted oxygen-bearing stream by combining said depleted oxygen-bearing stream with said oxygen-bearing feedstream.

4. A process according to claim 1 wherein said catalyst comprises said alkaline earth metal oxide catalyst and is impregnated on a refractory metal oxide support.

5. A process according to claim 4 wherein said refractory metal oxide support is selected from the group consisting of alumina, silica, silica-alumina, and titania.

6. A process according to claim 4 wherein said catalyst further comprises an alkali metal oxide.

7. A process according to claim 6 wherein said alkaline earth metal oxide is magnesium oxide and said alkali metal oxide is sodium oxide.

8. A process according to claim 7 wherein said at least one mercaptan has from 1 to 8 carbon atoms per molecule.

9. A process according to claim 7 wherein said oxygen-bearing feedstream consists essentially of oxygen and nitrogen, said oxygen-bearing feedstream is contacted countercurrently with said mercaptan-based feedstream and said process further comprising recycling said depleted oxygen-bearing stream by combining said stream depleted oxygen-bearing with said oxygen-bearing feedstream.

10. A process according to claim 1 wherein the catalyst is said basic form of macroreticular polystyrene-divinyl benzene copolymer.

11. A continuous process for producing at least one disulfide comprising the steps of:
 (a) continuously feeding at least one mercaptan in a mercaptan-based feedstream into a reactor containing a catalyst selected from the group consisting of (a) alkaline earth metal oxides on a refractory metal oxide support, (b) alkaline earth metal oxides in combination with alkali metal oxides on a refractory metal oxide support, and (c) a polymer consisting essentially of a basic form of macroreticular polystyrene-divinyl benzene copolymer;
 (b) continuously feeding a stream comprising oxygen and nitrogen into the reactor so as to contact the mercaptan-based feedstream in a countercurrent manner;
 (c) continuously removing unreacted oxygen and nitrogen from said reactor and recycling them back into said reactor;
 (d) continuously recycling unreacted mercaptans back into said reactor;
 (e) continuously recovering a product stream comprising at least one disulfide form said reactor; and
 (f) maintaining a reaction pressure in the range of about 1 to about 11 atmospheres.

12. A continuous process for making disulfides comprising the steps of:
 (a) continuously reacting in a reaction zone a mercaptan-based feedstream and an oxygen-bearing feedstream in the presence of a catalyst selected from the group consisting of (1) alkaline earth oxides on a refractory metal oxide support, (2) alkaline earth oxides and alkali metal oxides in combination on a refractory metal oxide support, and (3) a basic form of macroreticular polystyrene-divinyl benzene copolymer thereby producing a continuous water-bearing disulfide product stream and a depleted oxygen-bearing stream;
 (b) separating said continuous water-bearing disulfide product stream into an oil-phase stream and a water-phase stream;
 (c) separating said oil-phase into a mercaptan-based stream and a disulfide-based stream;
 (d) recycling said mercaptan-based stream by combining with a mercaptan feedstream thereby forming the mercaptan-based feedstream of (a); and
 (e) separating the disulfide-based stream of (c) into a disulfide product stream and a heavier product stream.

13. A process according to claim 2 wherein said mercaptan-based feedstream and said oxygen-bearing feedstream are contacted countercurrently and said reaction zone is externally cooled.

14. A process according to claim 13 wherein said oxygen-bearing feedstream consists essentially of oxygen and inert gas.

15. A process according to claim 14 wherein said alkaline earth oxide is magnesium oxide and said alkali metal oxide is sodium oxide.

16. A process according to claim 15 wherein said separation step of (c) is performed by distillation.

17. A process according to claim 16 wherein said separation step of (e) is performed by distillation.

18. A process according to claim 17 further comprising recycling said depleted oxygen-bearing stream of (a) by combining with an oxygen stream thereby forming said oxygen-bearing feedstream of (a).

19. A process according to claim 18 wherein said mercaptan-based feedstream consists essentially of methyl mercaptan.

20. A process according to claim 12 wherein said mercaptan-based feedstream consists essentially of methyl mercaptan.

21. A process according to claim 4 wherein said alkaline earth oxide is magnesium oxide.

* * * * *

UNITED STATES PATENT AND TRADEMARK OFFICE
CERTIFICATE OF CORRECTION

PATENT NO. : 5,202,494
DATED : April 13, 1993
INVENTOR(S) : John S. Roberts et al It is certified that error appears in the above-identified patent and that said Letters Patent is hereby corrected as shown below:

Column 6, line 55, between "and" and "inert", please delete "in" and insert therefor --- an ---.

Column 8, line 20, please delete "claim 2" and insert therefor --- claim 12 ---.

Signed and Sealed this

Twenty-eighth Day of December, 1993

Attest:

BRUCE LEHMAN

*Attesting Officer*     *Commissioner of Patents and Trademarks*